United States Patent [19]

Brazinsky

[11] Patent Number: 5,316,761
[45] Date of Patent: May 31, 1994

[54] COSMETIC GEL STICK COMPOSITIONS

[75] Inventor: Judy Brazinsky, Kearny, N.J.

[73] Assignee: Bristol-Myers Squibb Company, New York, N.Y.

[21] Appl. No.: 852,588

[22] Filed: Mar. 17, 1992

Related U.S. Application Data

[63] Continuation of Ser. No. 504,497, Apr. 4, 1990, abandoned.

[51] Int. Cl.$^5$ .......................... A61K 07/32; A61K 7/48
[52] U.S. Cl. ................................. 424/65; 424/DIG. 5
[58] Field of Search ...................... 424/65, 68, DIG. 5, 424/944

[56]         References Cited
U.S. PATENT DOCUMENTS

| | | | |
|---|---|---|---|
| 4,268,498 | 5/1981 | Gedeon et al. | 424/59 |
| 4,759,924 | 7/1988 | Luebbe et al. | 424/42 |
| 4,944,938 | 7/1990 | Potini | 424/68 |
| 4,948,578 | 8/1990 | Burger et al. | 424/68 |

*Primary Examiner*—Dale R. Ore
*Attorney, Agent, or Firm*—Charles J. Zeller

[57]            ABSTRACT

A clear cosmetic gel stick composition consisting essentially of from about 60 to about 90% of an aliphatic polyhydric alcohol having from 2 to 6 carbons and from 2 to 6 hydroxyl groups; from about 3 to about 8% soap; from about 1 to about 7% of a water-soluble emollient that is polyoxyalkylene ether of a fatty alcohol, the alcohol moiety having from about 8 to about 22 carbons and the number of alkylene glycol ether units having an average value of at least about 20; from about 1 to about 5% of a water-dispersible emollient that is a polyoxyethylene ether of a branched chain fatty alcohol, the fatty alcohol moiety having from about 8 to about 22 carbons and the average number of ethylene glycol ether units being from 1 to about 6; from about 10 to about 20% water, and an amount of an alkalinity agent effect to substantially prevent crystal growth.

11 Claims, No Drawings

COSMETIC GEL STICK COMPOSITIONS

This is a continuation-in-part application of U.S. Ser. No. 07/504,497 filed Apr. 4, 1990, now abandoned.

FIELD OF INVENTION

This invention relates to gel stick compositions that are especially clear. More specifically, this invention concerns transparent gel stick compositions that are suitable for various cosmetic utilities, including that of a deodorant stick composition. Most specifically, the invention of the present application relates to transparent cosmetic stick compositions containing a branched chain alkoxylated emollient of limited solubility in water in combination with a water-soluble alkoxylated emollient. In particular, this invention concerns such transparent cosmetic stick compositions that contain excess alkali in order to prevent crystal growth.

BACKGROUND OF THE INVENTION

Gelled compositions in stick form are well known and have been used for various cosmetic and pharmaceutical applications. The gel sticks should be of such firmness that a reasonable amount of active ingredients is applied when the stick is rubbed over the skin. Transparent gel stick compositions are also known and may be preferred by consumers, perhaps because they regard the clarity as an indication of product purity or performance.

Thus, U.S. Pat. No. 4,759,924 to Luebbe et al discloses cosmetic stick compositions comprising about 40–70% of a polyhydric aliphatic alcohol; about 3–10% soap; about 1–20% hydroalcoholic soluble emollient and water, the emollient having the formula $R(OC_3H_6)_a(OC_2H_4)_bOH$ wherein $a/(a+b) \leq 0.5$. Optionally, the compositions also may contain less than about 12.5% of a short chain monohydric alcohol such as ethanol and up to about 10%, preferably 1–5% of a water-insoluble emollient.

The water-insoluble emollients disclosed in the Luebbe patent are fatty esters, fatty ethers, alkoxylated fatty esters, fatty alcohols and low molecular weight silicone fluids. Typical materials include isopropyl palmitate, myreth-4, PEG-8-distearate, cetyl alcohol, dimethicone copolyol, cyclomethicone and dimethicone.

A clear stick formulation is also disclosed in de Navarre, The Chemistry and Manufacture of Cosmetics, Vol. IV, p. 697 (Second Edition 1975). The de Navarre composition contains 15% Pluronic F-127 (a polyoxyethylene, polyoxypropylene block copolymer); 7% sodium stearate; 68% propylene glycol and water. However, the de Navarre formulation does not contain a water-insoluble emollient. Moreover, the formulation of de Navarre is exceptionally hard.

Cosmetic gel stick compositions are also disclosed in GB 2,114,887, which compositions comprise 2–60% of an alkanol having 1–4 carbons; 2–50% of a diol having 4 carbons, and 2–15% soap, the composition having an average melting point of at least 50° C. The compositions of the GB '887 application may also contain an ethylene oxide and/or propylene oxide condensation product of the formula $H(C_2H_4O)_a(C_3H_6O)_bOR$ where R is either hydrogen or an alkyl group having from 1 to 20 carbons and a and b are each from 0 to 35, the sum of a+b not exceeding 35. There is no indication that the formulations of GB '887 are clear.

Gelled deodorant compositions are also disclosed in Appell, Cosmetics, Fragrances and Flavors, p. 62 (1982).

U.S. Pat. No. 4,268,498 to Gedeon et al discloses clear cosmetic sticks containing 2–5% polyoxyethylene (17–23)-glucose fatty acid ester; 2–5% polyoxyethylene (20–26) ether of a long chain alcohol; 24–72% polyoxypropylene (2–5) ether of a long chain alcohol; 5–8% sodium salt of a fatty acid; 5–10% propylene glycol; 5–10% lower alkyl ester of a fatty acid; 2–5% water, and 3–40% of a cosmetically active ingredient.

Aqueous gel compositions containing a water-insoluble pharmaceutically or cosmetically active organic ingredient employing as gelling agents certain polyoxyethylene/polyoxypropylene block copolymers are disclosed in Schmolka, U.S. Pat. No. 3,867,533. U.S. Pat. No. 4,089,814, also to Schmolka, discloses a roll-on perfume composition comprising per 100 parts by weight of composition, 5–15 parts essential oil; 25–40 parts alcohol; 20–40 parts certain polyoxyethylene-polyoxypropylene block copolymers, and 5–50 parts water.

A solid, transparent, gelled antiperspirant composition is disclosed in U.S. Pat. No. 4,154,816 to Roehl et al, the compositions of Roehl containing a lower monohydric alcohol, a di- and/or trihydric alcohol and/or a lower polyglycol, a propylene-ethylene glycol polycondensate having the formula $HO(C_2H_4O)_x(C_3H_6O)_yH$ wherein $y/(x+y)=0.6$ to 1 and have a molecular weight of at least 500; dibenzaldehydemonosorbitol acetal; an antiperspirant compound, and mono- or dialkylolamide of a higher fatty acid.

Cosmetic stick compositions containing an active are also disclosed in U.S. Pat. No. 4,226,889 to Yuhas, the compositions containing by weight 1–30 parts sodium stearate; 100 parts water and the active material. Preferably, the composition also contains a polyhydroxyl compound such as a glycol or polyglycol in an amount of from 0.5–10% by weight of the composition.

U.S. Pat. No. 4,346,079 to Roehl discloses antiperspirant compositions containing dibenzaldehyde-monosorbitol acetal as a gelling agent and up to only about 10% of propylene-ethylene polycondensate. A solid antiperspirant stick composition is also disclosed in U.S. Pat. No. 4,425,328 to Nabial, the base compositions containing hydrophobic waxy matrixes including a volatile silicone emollient, the level of which may be reduced by incorporation of certain liquid polyoxypropylene-alkyl ethers.

U.S. Pat. Nos. 4,382,079 and 4,440,742, both to Marschner, disclose deodorant stick compositions containing a bicarbonate. In addition to the bicarbonate, the Marschner compositions contain a soap-based gel comprising 20–90% polyhydric alcohol gelled by about 2–15% of an alkali metal salt of a $C_{14}$–$C_{20}$ saturated fatty acid. Other optional ingredients include soaps, emollients and emulsifiers such as silicones, fatty esters, fatty amines, fatty alcohols, ethoxylated fatty alcohols and acids, thickeners and bacteriostats. The compositions of Marschner are said to be clear, notwithstanding the incorporation of the bicarbonate. Thus, the composition of Example 16 containing 8% potassium bicarbonate is reported to have similar appearance to the composition of Example 15, which has no bicarbonate.

Clear aqueous gels prepared from certain polyoxybutylene-polyoxyethylene block copolymers are disclosed in U.S. Pat. No. 4,465,663 to Schmolka. Cosmetic sticks comprising polyhydric aliphatic alcohols, ethylene oxide and/or propylene oxide condensation products, and soap are disclosed in U.S. Pat. No. 4,504,465 to Sampson et al.

A nonstaining antiperspirant stick composition is disclosed in U.S. Pat. No. 4,511,554 to Geria et al. Other antiperspirant/deodorant stick compositions are disclosed U.S. Pat. No. 4,524,062 to Laba et al and U.S. Pat. No. 4,720,381 to Schamper et al. Clear acid stable dibenzyl monosorbitol acetal gels are disclosed in U.S. Pat. No. 4,725,430 to Schamper et al. A transparent gel base is disclosed in GB 1,207,438, the composition comprising 47–75% of a mixture of alkylene oxide block polymers and fatty alcohol polyethylene glycol ethers and/or alkyl-phenol-polyethylene glycol ethers. Cosmetic gels are also disclosed in GB 2,020,974 A and GB 2,114,887 A.

A nonaqueous deodorant stick composition is disclosed in Canadian Patent 1,196,867 to Geria.

Notwithstanding the array of prior art in the field of cosmetic compositions, the gel compositions designated as clear or translucent do not have the degree of clarity desirable in such products. Moreover, many of the prior art products tend to become cloudy or hazy after standing for a period of time. Typically, the haziness becomes progressively worse, so that after about a month or so the product is quite cloudy and can be said to have little or no transparency. Inasmuch as products such as these are often warehoused for one or more months subsequent to manufacture, the length of time the product retains at least the major portion of its transparency is an important characteristic.

Another problem associated with gelled sticks of the type herein disclosed in the formation of crystals over time. These crystals are particularly noticeable in view of the clarity of the product, and are believed caused by impurities contained in the soap component.

SUMMARY OF THE INVENTION

It is an object of the present invention to provide a clear gel stick composition suitable for use in cosmetic applications, especially deodorant products.

It is a further object of the present invention to provide such a stick composition that has a length of life in excess of about one month.

It is yet another object of the present invention to prevent the growth over time of visible crystals in the clear gelled stick product.

The cosmetic gel stick compositions of the present invention comprise from about 3 to about 8% soap; from about 1 to about 7% water soluble polyoxyalkylene ether of a fatty alcohol; from about 1 to about 5% polyoxyalkylene ether of a branched chain fatty alcohol, said ether having limited solubility in water; from about 10 to about 20% water, and from about 60 to about 90% aliphatic polyhydric alcohol having from 2 to 6 carbons and from 2 to 6 hydroxyl groups. The polyoxyalkylene ethers are functionally incorporated as emollients, and generally are polyoxyethylene ethers. In some instances, however, polyoxyethylene, polyoxypropylene ethers of fatty alcohols having less than about 20 mol percent polyoxypropylene based on the total mols of polyoxyalkylene might also be suitable.

It has further been found that a small amount, typically between about 0.001 to about 2% by weight of the composition of an alkali material, for example, an alkanolamine, alkali metal hydroxide or other base, is effective to substantially prevent the growth of visible crystals within the clear gelled stick product.

DETAILED DESCRIPTION OF THE INVENTION

The clarity of gel stick compositions has been found to be improved by incorporating into the composition an amount of a polyoxyethylene ether of a branched chain fatty alcohol effective to provide transparency, as defined below. The ether of the branched fatty alcohol is an emollient that has limited solubility in water, and is hereinafter referred to as the "water dispersible emollient." This designation, however, is not intended to rule out the use of materials typically categorized as water-insoluble, inasmuch as the terms "water-insoluble" and "water-dispersible" are not quantitatively exact. In this regard ample definition of the suitable ethers of branched fatty alcohols is provided below.

Suitable water-dispersible emollients are those polyoxyethylene ethers whose branched fatty alcohol moiety typically has from about 8 to about 22 carbon atoms. Preferably, the fatty alcohol moiety has 14 to 20 carbons, most preferably 18 carbons. The average number of ethylene glycol ether units is from 1 to about 6, preferably from 1½ to about 4, most preferably from about 2 to about 3. As the number of ethylene glycol ether repeating units increases, the material will become increasingly dispersible in water. Accordingly, care must be used when using the water-dispersible emollients that have an average number of glycol ether units of about 4 and above. The preferred water-dispersible emollient is the polyoxyethylene ether of isostearyl alcohol having two ethylene glycol ether units, this material also being called Isosteareth-2 in the CTFA Cosmetic Ingredient Dictionary (Third Edition 1982). Using the CTFA nomenclature, other suitable materials are Isodeceth-4, Isodeceth-5, Isolaureth-3, Isosteareth-3, and Isosteareth-6.

The water-dispersible emollient is present in an amount of from about 1 to about 5%, preferably 2 to about 4% by weight of the composition. Its hydrophobic-lipophilic balance (HLB) is less than about 10–11, which is the region between water dispersibility and water solubility. Preferably, the HLB is between about 4 to about 9.

The second essential ingredient in the compositions of the present invention is a water-soluble emollient. Suitable water-soluble emollients are polyoxyethylene ethers of fatty alcohols having a sufficient number of ethylene glycol ether units to provide solubility. Preferably, these water-soluble emollients have in excess of an average of about 20 ethylene glycol ether units, most preferably in excess of 35 such units. The fatty alcohol moiety will have from about 8 to about 22 carbons, preferably from about 14 to about 18 carbons, most preferably 18 carbons. Especially suitable as the water-soluble emollient is polyoxyethylene ether of stearyl alcohol having 100 ethylene glycol ether units. The CTFA Dictionary nomenclature for this material is Steareth-100. Using the nomenclature of the CTFA Dictionary, other suitable materials are Ceteareths-20, 25, 30, 50 and 55; Ceteths-20, 25 and 45; Cetoleth-25; Laureths-25, 30 and 40; Oleths-25 and 50, and Steareths-20, 30, 40, 50 and 100. Polyoxyethylene, polyoxypropylene ethers of fatty alcohols having less than about 20 mol percent polyoxypropylene may also be suitable in some instances, the fatty alcohol moiety being as defined above. Also suitable are polyoxyethylene glycols having from about 20 to about 200 mols ethylene oxide per molecule. Typically, the HLB value of the water soluble emollient will be above about 12, preferably from about 15 to about 20.

The water-soluble emollient is present in an amount of from about 1 to about 7%, preferably from about 2 to about 5% by weight of the composition.

The compositions of the present invention also include an alkali metal fatty acid soap such as sodium stearate, sodium laurate, sodium myristate, palmitate, and potassium cocoate. The soaps are contained in the composition of the present invention in an amount of from about 3 to about 8%, preferably from about 4 to about 6% of the weight of the composition.

An organic solvent is also an essential ingredient of the subject invention. The solvent of choice is propylene glycol, although other polyhydric aliphatic alcohols having from 2 to 6 carbons, preferably 2 or 3 carbons, may be used. In addition to propylene glycol, ethylene glycol, glycerin and sorbitol are suitable. The organic solvent is present in an amount of from about 60 to about 90%, preferably from about 70 to about 85% by weight of the composition.

The last essential constituent is water, which is present in an amount of from 10 to about 20%, preferably from about 12 to about 18% by weight of the composition.

The compositions of the present invention are transparent to the transmission of light. By transparent is meant that sufficient light passes through the gel sticks of the present invention to enable an observer to see without difficulty an image, e.g., lettering, placed at the rear of the gel stick. Generally, gel sticks in accordance with the present invention will transmit more than 40% of the light passed through, the percentage of light transmission being obtained by the procedure set forther in Example 1.

Preferably, more than 50% of the light will pass through using the protocol of Example 1. Most preferably, 60% or more of the light will pass through, such products being exceptionally clear. Moreover, the gel sticks of the present invention remain transparent for a reasonable period of time, typically at least about one month at room temperature preferably for at least three months at room temperature.

However, it has been found that over time crystals sometimes appear in the product. These crystals may be small—less than about 1/32 inch in size—or may be quite large, with a maximum size of about 3/16 inch. The crystals do not affect clarity or product performance, but are visible and may be deemed objectionable by some consumers. These crystals tend to appear after about three to six months, but do not occur with every lot of product. For this reason it is believed that the growth of the crystals is caused by impurities in one or more of the gel composition raw materials, most likely in the soap constituent.

We have found that crystal growth is substantially, often completely, avoided by incorporating an effective amount of an alkali material, for example, an ammonium or alkali metal hydroxide, especially sodium hydroxide; an alkanolamine, e.g., mono-, di- and triethanolamine. Triethanolamine is preferred. The alkali material is present in an amount effective to make the product composition crystal-free. By crystal-free as used herein is meant a cosmetic gel stick product in which crystals substantially do not occur within one month of storage at 115° F. or within six months of storage at 20° C.

The effective amount of alkali material is dependent on whether it is a strong or weak base. Strong bases require low levels of the alkalinity material, generally less than 0.1% by weight, while weak bases may be present in a level of up to even 2% by weight of the total composition. The effective amount of the alkalinity agent ranges from about 0.001 to about 0.1%, preferably from about 0.005 to about 0.05% in the case of a strongly basic material, and from about 0.1 to about 2%, preferably 0.5 to about 1.5%, in the case of a weakly basic material.

PLEASE CAREFULLY REVIEW THESE CONCENTRATIONS.

In addition to clarity, the products of the present invention must have sufficient hardness so that they may be applied without damage to the stick. On the other hand, a sufficient amount of the composition must adhere to the skin when the stick composition is used on skin. Typically, the stick compositions of the present invention will have a hardness of from about 2 to about 6, preferably from about 2.5 to about 4.5, as measured on a Chatillon Gauge, Model No. DPP-5, at a speed setting where the product being tested is propelled upwards at a speed of 3 cm/min. The product stick is then raised one inch above the top of its package and centered under the cutter along the longitudinal axis of the ellipse. A cut of 30 seconds is made, and the hardness reading from the gauge is obtained.

Adjuvants include coloring agents, fragrance agents, and bacteriocides. Each of these adjuvants is included in an amount suitable to obtain its requisite function, typically less than about 1% by weight of the composition. Suitable coloring agents are the FD&C grade dyes such as FD&C Blue #1 and FD&C Yellow #5. The dye is typically present in the range of from about 0.01 to 1%, preferably 0.01 to 0.1% by weight. The dye concentration, however, should not be so high as to render the product opaque. Emollients such as isopropyl stearate, isopropyl myristate, isobutyl myristate and the like may be included at low levels, typically less than about 1% by weight of the composition, to improve feel properties. The compositions of the present invention may also include a deodorant material. Suitable deodorant materials include bacteriostatic quaternary ammonium compounds such as cetyltrimethyl ammonium bromide, cetylpyridinium chloride, di-isobutylphenoxyethoxy ethyl dimethyl benzyl ammonium chloride, N-alkylpyridinium chloride, sodium N-lauroyl sarcosinate; stearyltrimethyl ammonium chloride and 2,4,4'-trichloro-2'-hydroxydiphenyl ether, known as Triclosan. Deodorants, if present, are generally included in an amount of from about 0.05 to about 1% by weight of the composition.

Low levels, less than 12.5%, preferably less than 5%, by weight of the composition of a low molecular weight alcohol may be also incorporated, e.g., ethanol.

The compositions of the present invention are made by admixing the various ingredients together in the liquid state, materials otherwise solid at room temperature being melted before, during or after addition, pouring the liquid mixture into a mold, and thereafter allowing the admixture to solidify.

The gel sticks are used by the consumer by rubbing the gel stick on the area of the body where application of the actives is desired. A deodorant stick, for example, is used by applying the stick to the axilla area to apply the deodorant agent.

The benefits of the compositions of the present invention are demonstrated in the examples below, which are not intended to be limiting. Unless otherwise indicated, all concentrations are on a weight basis and all ingredients are identified on a 100% actives basis.

EXAMPLE 1

The compositions set forth in Table I were prepared by first heating the propylene glycol to 180°–200° F. after which the Steareth-100 was added, with mixing, followed by the addition with mixing of the stearate soap and the water. After cooling slightly, the insoluble emollient is added, followed by further cooling, to about 140°–150° F. The remaining ingredients are then added, and the batch is cooled slightly, poured into containers, and cooled to room temperature.

TABLE I

| Constituent | Concentration (wt. %) | | |
|---|---|---|---|
| | A | B | C |
| Propylene glycol | 73.05 | 73.05 | 73.05 |
| Sodium stearate | 4.0 | 4.0 | 4.0 |
| Steareth-100(1)* | 5.0 | 5.0 | 5.0 |
| Isosteareth-2(2)* | — | 3.0 | — |
| Steareth-2(3)* | — | — | 3.0 |
| Deionized water | 13.5 | 13.5 | 13.5 |
| Triclosan | 0.25 | 0.25 | 0.25 |
| Perfume | 1.0 | 1.0 | 1.0 |
| FD&C Blue No. 1 (0.1% sol'n) | 0.2 | 0.2 | 0.2 |
| TOTAL | 100.0 | 100.0 | 100.0 |

*CTFA nomenclature.
(1)Polyethylene glycol ether of stearyl alcohol having 100 moles ethylene oxide per molecule. Water-soluble emollient having an HLB of about 18.8. Available as Brij 700 from ICI Americas, Inc.
(2)Polyethylene glycol ether of isostearyl alcohol having 2 moles ethylene oxide per molecule. Water-insoluble emollient having an HLB of about 4.6. Available as Arosurf 66-E2 from Sherex Chemical Co.
(3)Polyethylene glycol ether of stearyl alochol having 2 moles ethylene oxide per molecule. Water-insoluble emollient having an HLB of about 4.9. Available as Brij 72 from ICI Americas, Inc.

The Compositions A, B and C were evaluated for clarity by measuring the amount of light transmission through the gel product. The percent transmission varies with the wavelength of light. The wavelengths that define the range of minimum and maximum light transmission depends on the presence or absence of a dye in the gel stick, and the concentration of the dye if present. Thus, a colorless product would be expected to transmit more light than a dye-containing product. The percent light transmissoin also depends on the color of the dye. For the Compositions A, B and C, which contain a blue dye, the highest percent transmission occurring at about 800 nm and the lowest at about 400 nm. An intermediate wavelength of 600 nm was used in measuring light transmission, in accordance with the following procedure: 40 grams of molten composition was poured into a petri dish (Thomas Petri dish, 100 Mm diameter x 15 Mm deep) and allowed to cool and solidify at room temperature overnight. A spectral scan from 400 nm to 800 nm was taken and the transmission at 600 nm was measured.

For Composition A, which does not contain any water-insoluble emollient, the average transmission light was 9.15%. For Composition B, within the scope of the present invention and containing 3% Isosteareth-2, the average transmission of light was 73.95%. For Composition C, which is outside the scope of the present invention in that it contains a linear chain water-insoluble emollient, the average light transmission was 0.17%.

EXAMPLE 2

Composition B was evaluated for stability. The composition in its molten state was poured into a conventional deodorant stick container and then stored under various conditions as reported below.

| Test Conditions | Observed Clarity |
|---|---|
| 32° F. (1 Month) | Slight loss in clarity |
| Freeze/Thaw (5 cycles) | Slight loss in clarity |
| Room Temperature (3 months) | Crystal clear |
| 104° F. (3 months) | Crystal clear |
| 115° F. (1 month) | Some haze at the core |

EXAMPLE 3

Eight lots of sodium stearate (from the same manufacturer), all of which met the specifications for this raw material set by the industry and the manufacturer, were used in making Composition B of Example 1, namely, Compositions B-1 to B-8. Eight analogous compositions (Compositions B-1-TEA to B-8-TEA) were made except the level of propylene glycol was 72.05% and each of the compositions contained 1% triethanolamine (TEA). These compositions B-1 to B-8 and B-1-TEA to B-8-TEA were all stored at 115° F. for one month.

After storage at these conditions, all of the compositions B-1 to B-8 had crystals growing within the clear gel. On the other hand, none of the Compositions B-1-TEA to B-8-TEA showed any evidence of crystal growth.

EXAMPLE 4

The effect of triethanolamine level was studied. Composition B of Example 1 was prepared, except that propylene glycol level was decreased by an amount equal to the TEA incorporated. Compositions D-1 through D-5 were prepared and observed for crystal growth after one month's storage at 115°.

| Comp | TEA (%) | Comments |
|---|---|---|
| D-1 | 0.25 | Transparent; crystals formed |
| D-2 | 0.751 | Transparent; crystals formed |
| D-3 | 1.0 | Clear; no crystals |
| D-4 | 1.5 | Clear, no crystals |
| D-5 | 2.0 | Clear; no crystals |

EXAMPLE 5

Composition B-7 of Example 3 was modified by the addition of 0.01% sodium hydroxide (Composition B-7-OH-1) and 0.05% sodium hydroxide (Composition B-7-OH-2). Neither of these compositions gave evidence of crystal formation after one month at 115° F.

What is claimed is:

1. A transparent, essentially crystal-free cosmetic gel stick composition consisting essentially of by weight of the composition from about 60 to about 90% of an aliphatic polyhydric alcohol having from 2 to 6 carbons and from 2 to 6 hydroxyl groups; from about 3 to about 8% soap; from about 1 to about 7% of a water-soluble emollient selected from the group consisting of polyoxyethylene ethers of fatty alcohols, polyoxyethylene, polyoxypropylene ethers of fatty alcohols having less than 20 mol percent polyoxypropylene based on the total mols of polyoxyalkylene, and polyoxyethylene glycols having 20 to 200 mols ethylene oxide, the fatty alcohol moiety having from about 8 to about 22 carbons and the average number of alkylene glycol ether units being at least about 20; from about 10 to about 20% water; from about 1 to about 5% of a water-dispersible emollient that is a polyoxyethylene ether of a branched chain fatty alcohol, the fatty alcohol moiety having from about 8 to about 22 carbons and the average number of ethylene glycol ether units being from 1 to about 6, and an alkalinity material in an amount effective to prevent the growth of crystals in said transparent gel stick composition for a period of at least one month at 115° F.

2. In a transparent cosmetic gel stick composition containing an aliphatic polyhydric alcohol having from 2 to 6 carbons and from 2 to 6 hydroxyl groups; a soap; a water-soluble emollient selected from the group consisting of polyoxyethylene ethers of fatty alcohols, polyoxyethylene/polyoxypropylene ethers of fatty alcohols having less than 20 mol percent polyoxypropylene based on the total mols of polyoxyalkylene and polyoxyethylene glycols having 20 to 200 mols ethylene oxide, the fatty alcohol moiety having from about 8 to about 22 carbons and the average number of alkylene glycol ether units being at least about 20; water, and a water-dispersible emollient that is a polyoxyethylene ether of a branched chain fatty alcohol, the fatty alcohol moiety having from about 8 to about 22 carbons and the average number of ethylene glycol ether units being from 1 to about 6, said cosmetic gel stick composition characterized by crystal-growth formation upon aging wherein the improvement comprises incorporating in said composition of an alkalinity material in an amount effective to prevent the growth of said crystals in said transparent gel stick composition for a period of at least one month at 115° F.

3. The composition of claim 1 or 2 wherein the alkalinity agent is an ammonium or alkali metal hydroxide in an amount of above about 0.001% by weight of the composition.

4. The composition of claim 3 wherein the alkalinity agent is present in an amount of from about 0.005 to about 0.1% by weight of the composition.

5. The composition of claim 4 wherein the alkalinity agent is triethanolamine.

6. The composition of claim 3 wherein the water-dispersible emollient is a polyoxyethylene ether of a fatty alcohol having an average of from 1½ to about 4 ethylene glycol ether units.

7. The composition of claim 6 wherein the water-soluble emollient is a polyoxyethylene ether of a fatty alcohol having in excess of 35 ethylene glycol ether units, wherein the polyhydric alcohol is propylene glycol, and wherein the soap is an alkali metal fatty acid soap having from 14 to 22 carbons per molecule.

8. The composition of claim 1 or 2 wherein the alkalinity agent is a mono-, di- or trialkanolamine present in an amount of above about 0.1% by weight of the composition.

9. The composition of claim 8 wherein the alkalinity agent is present in an amount of form about 0.1 to about 2% by weight of the composition.

10. The composition of claim 8 wherein the water-dispersible emollient is a polyoxyethylene ether of a fatty alcohol having an average of from 1½ to about 4 ethylene glycol ether units.

11. The composition of claim 10 wherein the water-soluble emollient is a polyoxyethylene ether of a fatty alcohol having in excess of 35 ethylene glycol ether units, wherein the polyhydric alcohol is propylene glycol, and wherein the soap is an alkali metal fatty acid soap having from 14 to 22 carbons per molecule.

* * * * *